United States Patent
Fisher et al.

(10) Patent No.: US 6,592,608 B2
(45) Date of Patent: Jul. 15, 2003

(54) BIOABSORBABLE SEALANT

(75) Inventors: John S. Fisher, Belleair, FL (US); Frederick Ahari, Tucson, AZ (US); Lucjan J. J. Hronowski, Bedford, MA (US)

(73) Assignee: Biopsy Sciences, LLC, Clearwater, FL (US)

(*) Notice: Subject to any disclaimer, the term of this patent is extended or adjusted under 35 U.S.C. 154(b) by 0 days.

(21) Appl. No.: 09/683,282

(22) Filed: Dec. 7, 2001

(65) Prior Publication Data

US 2003/0109899 A1 Jun. 12, 2003

(51) Int. Cl.$^7$ ................................................ A61D 1/00
(52) U.S. Cl. ...................................... 606/213; 606/214
(58) Field of Search ........................... 606/213, 214, 606/230; 604/197, 187; 528/354, 408; 525/411; 424/443; 404/444

(56) References Cited

U.S. PATENT DOCUMENTS

| | | | | |
|---|---|---|---|---|
| 2,576,576 A | * | 11/1951 | Cresswell | 606/229 |
| 3,942,532 A | * | 3/1976 | Hunter et al. | 606/231 |
| 3,954,635 A | * | 5/1976 | Cummings et al. | 252/8.82 |
| 4,027,676 A | * | 6/1977 | Mattei | 606/230 |
| 4,857,602 A | * | 8/1989 | Casey et al. | 525/408 |
| 5,851,229 A | * | 12/1998 | Lentz et al. | 623/23.72 |
| 6,071,301 A | * | 6/2000 | Cragg et al. | 606/213 |
| 6,086,607 A | * | 7/2000 | Cragg et al. | 606/213 |
| 6,090,130 A | * | 7/2000 | Nash et al. | 606/213 |
| 6,162,241 A | * | 12/2000 | Coury et al. | 606/214 |
| 6,165,201 A | * | 12/2000 | Sawhney et al. | 606/214 |
| 6,179,862 B1 | * | 1/2001 | Sawhney | 606/214 |
| 6,190,400 B1 | * | 2/2001 | Van De Moer et al. | 606/213 |
| 6,372,248 B1 | * | 4/2002 | Qin et al. | 424/443 |

* cited by examiner

Primary Examiner—Michael J. Milano
Assistant Examiner—P Roberts
(74) Attorney, Agent, or Firm—Ronald E. Smith; Smith & Hopen, P.A.

(57) ABSTRACT

Openings in a mammalian body made by any medical procedure or non-medical event are sealed with a bioabsorbable plug or sewn with a bioabsorbable suture. In one exemplary embodiment, the plug in dehydrated, unexpanded condition is pushed by a pushing device through the lumen of a needle until a first part of the plug is external to the opening and a second part is internal to the opening. The needle is then withdrawn while the position of the pushing device is maintained. The pushing device is then withdrawn, leaving the plug in sealing relation to the opening. The body's moisture causes the plug to expand to complete the sealing of the opening, or the expansion may be caused by exposure to air, light, or other stimulant. The opening may be formed in soft tissue, internal organs, or hard tissue. The plug seals the flow of liquid or gaseous biological fluids.

1 Claim, 13 Drawing Sheets

BIOABSORBABLE SEALANT

BACKGROUND OF INVENTION

1. Field of the Invention

This invention relates, generally, to the medical arts. More particularly, it relates to means for sealing openings in a mammalian body created by any means.

2. Description of the Prior Art

Openings may be formed in a human or other mammalian body by numerous means. Needles or other medical instruments may create puncture or other types of openings, for example. Moreover, electrical, ultrasound, optical instruments and the like may create openings. Gunshot and knife wounds and numerous other events may also cause openings to be formed.

An opening in a lung is undesirable because air leaks therefrom and causes the lung to collapse. However, openings in soft tissue, as well as openings in internal organs, such as the heart, kidney, liver, etc., also require closure. Openings in bones, cartilage, ligaments, and other hard tissue must also be closed.

Many techniques have been developed for the surgical closing of openings. Sutures were invented long ago, for example. One important drawback to using sutures in some applications arises from the fact that the needle used to sew the suture in place typically has a diameter that is larger than the suture. Thus, if a suture is used to close an opening in a lung, for example, air can escape from the lung in the space that surrounds the suture, i.e., the space has the diameter of the needle and is not fully occupied by the suture. This problem is addressed by applying an adhesive over the suture; when the adhesive cures, the openings around the suture are sealed. However, adhesives are difficult to apply and control and require time to cure.

Another more recently developed technique for closing openings includes the use of staples. The force required to apply staples may result in torn tissue. One solution to this problem is to apply an adhesive over the staples to seal the torn areas, just as is done in connection with sutures.

Adhesive have been used to close other openings in the body as well. Laparoscopic and endoscopic procedures, for example, may require sophisticated instrumentation. In situ curing of adhesives may be problematic depending upon the application, and may require the use of curing agents and other means for cross-linking free radicals to form the required bond. The curing agent may be air, visible light, ultraviolet light, heat, laser beams, chemical compounds that require mixing with one another, and so forth.

It would be advantageous therefore, if means for closing an opening could be found that did not rely upon adhesives and curing agents.

Numerous medical procedures and even non-medical events can result in openings in the body that need to be sealed, as mentioned earlier. Openings must be closed not just to stop the escape of air from the lungs, but to also stop the escape of body fluids from other body parts. Sealing means for closing openings are needed to stop the flow of blood, cerebral spinal fluid, and other fluids.

For exemplary purposes, an opening made by a biopsy needle will be considered. In a biopsy procedure, a needle adapted to collect tissue is inserted into a suspected lesion, usually multiple times. When a sufficient quantity of the lesion has been collected, it is taken to a lab for analysis.

To perform the procedure, a coaxial needle is first inserted so that its leading end is positioned near the suspected lesion. A biopsy needle is then inserted through the coaxial needle.

The puncture opening made by the coaxial needle may close and heal naturally if the lesion is in soft tissue such as a breast. However, if a lesion is in the lung, the puncture opening made by the coaxial needle may need to be closed quickly. The use of sutures or adhesives, or sutures and adhesives, are well-known as already mentioned, but such techniques have limitations.

What is needed, then, is an apparatus for closing an opening in a lung or other vascular organ as well as in soft or hard tissue. The needed apparatus should close an opening quickly but should not cause problems of the type associated with adhesives.

Physicians often have a need to re-visit a surgical procedure site to monitor a patient's recovery. However, the sutures and adhesives now in use include no means for helping a physician find the surgical site when a follow-up look is desired.

Thus there is also a need for a means that would enable a surgeon to locate a surgical site in the days, weeks, or months following a surgical procedure.

However, in view of the prior art considered as a whole at the time the present invention was made, it was not obvious to those of ordinary skill in the pertinent art how the identified needs could be fulfilled.

SUMMARY OF INVENTION

The long-standing but heretofore unfulfilled need for a method and apparatus for sealing openings made by medical or non-medical procedures in a mammalian body is now met by a new, useful, and nonobvious invention.

A first embodiment of the invention includes a plug formed of a preselected bioabsorbable material that expands in response to a predetermined stimulus. The plug is sized to fit within the opening prior to application of the predetermined stimulus to the dehydrated plug. The plug expands upon application of the predetermined stimulus thereto until the plug seals the opening. In this way, the plug, when expanded, prevents flow of liquid or gaseous fluid through the opening. The plug is gradually bioabsorbed as natural processes heal the opening. The preselected bioabsorbable material is a dehydrated hydrogel and the predetermined stimulus is moisture that is naturally present in the mammalian body.

The plug may have a solid, cylindrical configuration prior to application of the predetermined stimulus thereto so that the plug is adapted to fit into a lumen of a needle to facilitate introduction of the plug into the opening.

If the plug is to be employed as a scaffold for tissue regeneration, it may be provided in forms more suitable for that purpose. For example, it may have a corkscrew configuration at one end. It may also be designed to provide a mechanical anchor as well, having a leading end that expands radially outwardly after placement to prevent unintended outward migration of the plug.

The plug is impregnated with a contrasting agent to facilitate detection of the plug by imaging means selected from the group of imaging means consisting of magnetic resonance imaging, ultrasound, Doppler, and roentgenological means including x-ray, CT scan, mammography, and fluoroscopy.

Alternatively, the plug includes a radioactive substance detectable by a radiation detecting means including a gamma counter and a scintillation counter. In another alternative, the plug includes a transmitting means adapted to transmit signals in the electromagnetic spectrum that are detectable by receivers adapted to receive signals in the electromagnetic spectrum.

The plug is adapted to be slideably disposed in a lumen of a needle. A plug displacement means is adapted to abuttingly engage and slidingly displace the plug within the lumen to a preselected location near a distal end of the lumen. Withdrawal of the needle coupled with maintaining the plug displacement means at said preselected location during the withdrawal results in placement of the plug at the preselected location. Withdrawal of the plug displacement means does not cause displacement of the plug.

The novel material also has utility in promoting angiogenesis in a mammalian heart. A cavity or bore is formed in a heart and growth factor means is introduced into the bore. A bioabsorbable plug that expands in response to a predetermined stimulus then plugs the bore. The predetermined stimulus is applied to the bioabsorbable plug so that the bioabsorbable plug expands and seals the growth factor means within the bore.

The novel plug has further utility as a means for preventing loss of spinal fluid from the thecal sac. An opening is formed at a preselected site in the thecal sac by a biopsy needle introduced to the preselected site through a coaxial needle. The biopsy needle is withdrawn from the preselected site after the opening has been formed. A delivery catheter having a dehydrated, bioabsorbable plug formed of a preselected material that expands in response to a predetermined stimulus positioned in its lumen is then introduced through the coaxial needle to the preselected site. The dehydrated, bioabsorbable plug is pushed from the lumen of the catheter into the opening and said catheter is withdrawn from the preselected site. The bioabsorbable plug expands upon being hydrated by natural fluids present at the preselected site. The expansion holds the plug in place and further serves to prevent leakage of spinal fluid from the opening.

The novel material is not limited to plugs. For example, it may also be formed into a cylindrical member that slideably receives a plug. Such a cylindrical member and a plug may be used with one another to provide a means for sealing an incision in an artery. More particularly, a guide wire is inserted through the incision and a lumen of an introducer sheath is placed in receiving relation to the guide wire so that a leading end of the introducer sheath is guided to the incision by the guide wire. The leading end of the introducer sheath is positioned into abutting and surrounding relation to the incision. A dehydrated, bioabsorbable tube formed of a preselected material that expands in response to a predetermined stimulus is pushed from a lumen of the introducer sheath so that a leading end of the dehydrated, bioabsorbable tube is disposed in abutting and surrounding relation to the incision. The guide wire and the introducer sheath are then withdrawn from the artery. The leading end of a delivery catheter having an external diameter less than an internal diameter of the dehydrated, bioabsorbable tube is then introduced into the lumen of the dehydrated, bioabsorbable tube. A dehydrated, bioabsorbable plug formed of a preselected material that expands in response to a predetermined stimulus is positioned in a lumen of the delivery catheter and is pushed from said lumen into the lumen of the dehydrated, bioabsorbable tube. The delivery catheter is withdrawn and the dehydrated, bioabsorbable plug expands within the lumen of the dehydrated, bioabsorbable tube when contacted by natural moisture within the blood flowing through the artery. The dehydrated, bioabsorbable tube expands when contacted by the natural moisture within the blood and by natural moisture within tissue that surrounds the artery.

In another embodiment, an elongate suture is formed of a preselected bioabsorbable material that expands in response to a predetermined stimulus. The elongate suture is adapted to be pulled by a needle so that the elongate suture is used to sew closed the opening. The elongate suture has a diameter slightly less than a diameter of the needle, there being a clearance space about the elongate suture equal in diameter to the diameter of the needle less the diameter of the elongate suture. The elongate suture expands upon application of the predetermined stimulus thereto until the elongate suture seals the clearance space. The elongate suture, when expanded, prevents flow of liquid or gaseous fluid through the clearance space and is gradually bioabsorbed as the opening is healed by natural processes. The preselected bioabsorbable material is a hydrogel and the predetermined stimulus is moisture that is naturally present in a mammalian body. The elongate suture may be impregnated with a contrasting agent to facilitate its detection by imaging means selected from the group of imaging means consisting of magnetic resonance imaging, ultrasound, Doppler, and roentgenological means including x-ray, CT scan, mammography, and fluoroscopy. The elongate suture may include a radioactive substance detectable by a radiation detecting means including a gamma counter and a scintillation counter. Alternatively, it may include a transmitting means adapted to transmit signals in the electromagnetic spectrum that are detectable by receivers adapted to receive signals in the electromagnetic spectrum. Moreover, the elongate suture may be hollow and filled with a gaseous fluid.

A conventional suture, both bioabsorbable and nonbioabsorbable, may be coated with a material that expands in response to a predetermined stimulus and used in the same way as the suture made entirely of the novel material. This type of coating also provides a lubricious surface having a low coefficient of friction to minimize trauma during the suturing process.

A rigid medical staple of the type used in anastomosis of organs may also be coated with a preselected bioabsorbable material that expands in response to a predetermined stimulus to fill the openings made by the stapling procedure.

An important object of this invention is to provide a means for sealing openings in a mammalian body quickly and in the absence of conventional sutures, staples, and adhesives.

Another object is to provide a bioabsorbable means for sealing such openings.

Another major object is to provide a marking means that enables a physician to easily find a surgical site for follow-up purposes.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying diagrammatic drawings, in which:

FIG. 7C is a longitudinal sectional view of a plug that may be used as a "scaffold" for therapeutic drugs or the like;

DETAILED DESCRIPTION

Figure 1:
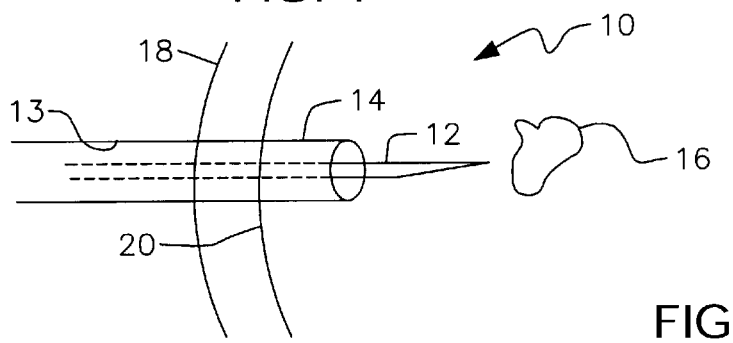
FIG. 1 is a side elevational view of a biopsy needle taking a sample from a lesion in a lung or any other soft tissue.

Referring to FIG. 1, it will there be seen that the reference numeral 10 denotes a biopsy site as a whole. Openings in a mammalian body may be formed by numerous other medical procedures and non-medical events as mentioned earlier. A biopsy procedure is explained just for exemplary purposes.

A biopsy needle 12 is ensleeved within lumen 13 of coaxial needle 14 when taking biopsy samples from lesion 16 because multiple entries and withdrawals of biopsy needle 12 are normally required. In the absence of coaxial needle 14, biopsy needle 12 would have to make multiple punctures of the patient's skin and lung during a biopsy procedure. Although coaxial needle 14 has a slightly larger diameter than biopsy needle 12, the trauma caused by one insertion of said coaxial needle is less than that of multiple biopsy needle insertions.

In the example if FIG. 1, the patient's skin is denoted 18 and the surface of the patient's lung is denoted 20. It should be understood, however, that the utility of this invention is not restricted to sealing openings formed in lungs by biopsy procedures but includes the sealing of openings formed by any means in the heart, brain, liver, kidneys, and even in hard tissue such as bone, cartilage, and the like.

When a sufficient amount of biopsy samples have been taken, biopsy needle 12 is withdrawn from coaxial needle 14.

Figure 2:
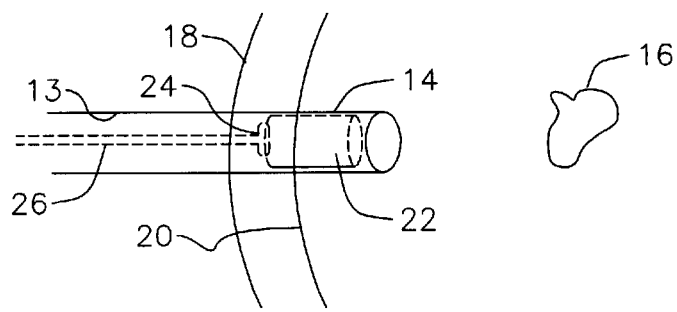
FIG. 2 is a view depicting the positioning of a bioabsorbable plug in the coaxial needle of FIG. 1.

As depicted in FIG. 2, a pusher assembly that includes a circular disc 24 and a rod 26 then slidingly introduces dehydrated plug 22 into lumen 13 of coaxial needle 14. In this first-described embodiment, plug 22 is of solid cylindrical construction, is about 2.5 cm in length, and is positioned approximately as shown in FIG. 2, i.e., a small extent of the plug is external to surface 20 of the lung and a larger extent thereof is inside the lung. This particular positioning is not critical and is depicted just to indicate that plug 22 is preferably a relatively long cylindrical plug, in this particular application, so that it is relatively easy to position in sealing relation to the puncture opening. The elongate extent of plug 22 provides a generous margin of error.

Figure 3:
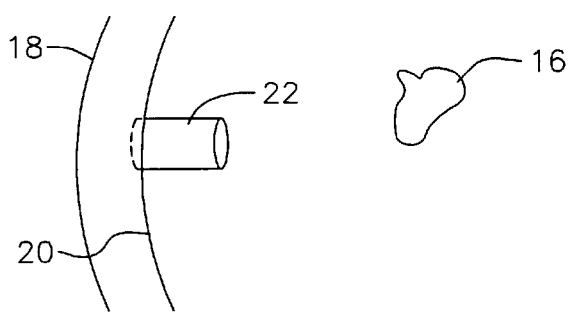
FIG. 3 is a view like that of FIG. 2, but after the coaxial needle has been withdrawn, leaving the bioabsorbable plug in sealing relation to a puncture wound.

FIG. 3 depicts biopsy site 10 after withdrawal of coaxial needle 14. Pusher disc 24 and rod 26 (FIG. 2) are held in place when coaxial tube 14 is withdrawn to ensure that plug 22 does not move. After coaxial tube 14 is fully withdrawn, pusher disc 24 and rod 26 are withdrawn to produce the view of FIG. 3.

Plug 22 is formed of a material that expands upon contact with a stimulant such as water, blood, air, visible light or other electromagnetic radiation such as a laser beam, a preselected chemical, and so on. In a preferred embodiment, the stimulant is moisture which is naturally present on the surface of a patient's lungs or other soft tissue, internal organs, or the like.

Figure 4:
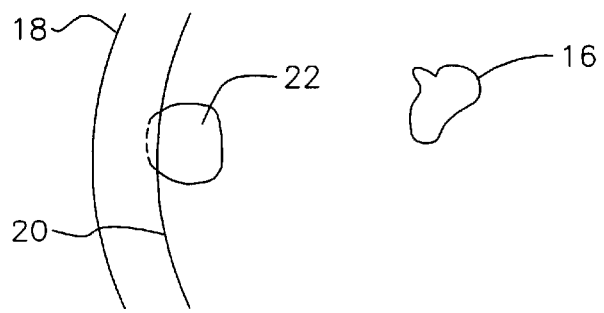
FIG. 4 is a view like that of FIG. 3, but depicting the plug in its enlarged configuration.

FIG. 4 depicts plug 22 shortly after its installation. It has been in contact with moisture, or other predetermined stimulant, for a few moments and the expandable material has expanded. The expansion effectively seals the peripheral edge of the puncture opening and prevents air from escaping the lungs. In other applications, the plug is used to stop bleeding or other liquid fluid flow from the liver, heart, thecal sac, etc.

Figure 5:
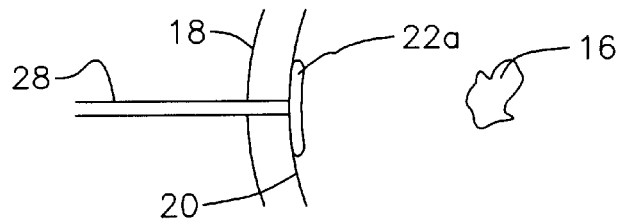
FIG. 5 is a view of an alternative embodiment where the bioabsorbable seal is positioned on an inside surface of a lung.

An alternative embodiment is depicted in FIG. 5. In this embodiment, bioabsorbable element 22a is releasably secured to the distal end of rod 28. Element 22a is diskshaped, having less longitudinal extent than bioabsorbable plug 22 of the first embodiment. Plug 22a has an unexpanded diameter that is preferably slightly greater than that of plug 22 so that it deploys to a diameter that is at least slightly greater than the diameter of the puncture wound when coaxial rod 14, not shown in FIG. 5, is retracted. Rod 28 is then retracted and separated from plug 22a when said plug 22a is firmly positioned in sealing relation to the inner wall of lung 20.

There are numerous means for interconnecting rod 28 and plug 22a such that said rod may be separated from plug 22a when said plug is firmly positioned in sealing relation to the puncture opening. An adhesive having a predetermined strength may be used, for example, and separation would occur upon applying a torque to rod 28 about its longitudinal axis.

Figure 6:
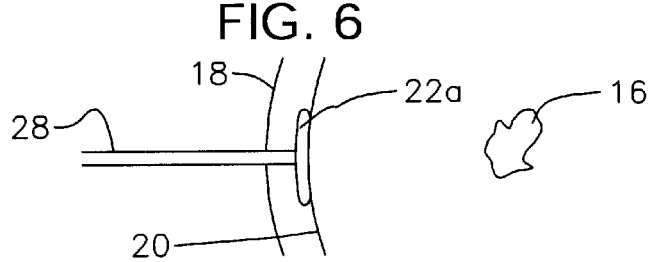
FIG. 6 is a view of an alternative embodiment where the bioabsorbable seal is positioned on an outside surface of a lung.

Another alternative embodiment is depicted in FIG. 6. This embodiment is much like the embodiment of FIG. 5 except that plug 22a is positioned in firmly sealing relation to the puncture opening on the exterior surface of the lung prior to separation of plug 22a and rod 28.

FIGS. 7A–H depict a few of the possible variations of plug 22. All of these plugs are in a dehydrated condition when positioned within lumen 13 of coaxial needle 14 and are expanded by contact with the body's natural moisture or by other means as mentioned earlier upon being pushed from said lumen by the earlier-mentioned pusher assembly.

Figure 7A:
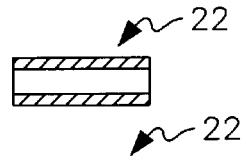
FIG. 7A is a longitudinal sectional view of a tubular plug.

In FIG. 7A, plug 22 is of tubular construction. This plug would not have utility in sealing an opening in a lung, obviously.

Figure 7B:
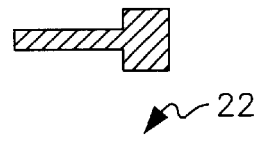
FIG. 7B is a longitudinal sectional view of a plug having an enlarged leading end.

Plug 22 of FIG. 7B has an enlarged anchor member 22b at its leading end. Anchor member 22b is compressed when plug is within lumen 13 and expands at least to some extent under its own bias upon emergence from said coaxial needle.

Figure 7C:
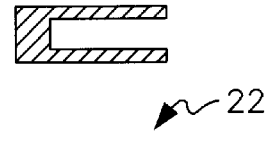

Plug 22 of FIG. 7C is generally "U"-shaped when seen in longitudinal cross-section as in said FIG. 7C.

Figure 7D:
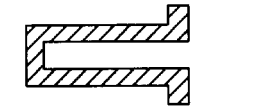
FIG. 7D is a longitudinal sectional view of another plug configuration having utility as a scaffold.

Plug 22 of FIG. 7D has a structure similar to that of FIG. 7C but further includes an outwardly turned flange 22c at its leading end. Flange 22c performs the same function as anchor member 22b of FIG. 7B, i.e. it prevents longitudinal travel of the plug in a direction toward the surface of the body, it being understood that the flange or anchor member is positioned in abutting relation to an interior side of an opening formed in an organ or other tissue.

Figure 7E:
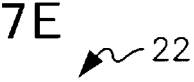
FIG. 7E is a longitudinal sectional view of another plug configuration having utility as a scaffold.
Figure 7F:
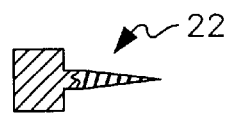
FIG. 7F is a longitudinal sectional view of another plug configuration having utility as a scaffold.
Figure 7G:
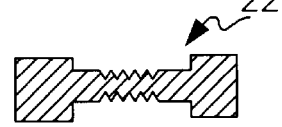
FIG. 7G is a longitudinal sectional view of another plug configuration having utility as a scaffold.

Plug 22 of FIG. 7E has an irregular or corkscrew leading end. FIG. 7F depicts a plug having a leading end in the configuration of a tapered corkscrew. Plug 22 of FIG. 7G includes a medal part of irregular configuration flanked by a leading and a trailing end of solid cylindrical configuration.

Figure 7H:
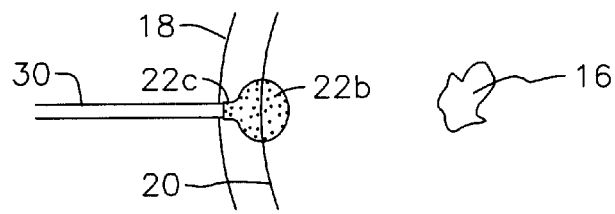
FIG. 7H is a view of an alternative, hollow bioabsorbable plug.

Significantly, the embodiments of FIGS. 7C–G enable plug 22 to serve as a "scaffold" upon which may be deposited growth hormone, stem cells, therapeutic drugs or any type, and so on. The increased surface area provides means for holding such therapeutic elements. Plug 22 or 22a may have a solid or hollow construction. The embodiment 22b of FIG. 7H is hollow and is filled with a gaseous fluid either just before or just after it is positioned in sealing relation to a puncture opening. The gaseous fluid is introduced into the hollow interior of plug 22b through rod 30, said rod being in fluid communication with balloon-like neck 22c of plug 22b. Plug 22b is expanded by gas introduction until it firmly seals the opening. Neck 22c is then sealed by any suitable means.

Alternatively, plug 22b is filled with a gaseous fluid prior to its use and neck 22c is sealed prior to introduction of the plug.

It should be understood that the lung is not the only internal organ of the body that may be punctured by a needle or other medical or non-medical device and require sealing. Openings formed in any vascular organs such as the kidneys, the liver, the heart, the brain, and the stomach, for example, may be sealed with the novel apparatus. Nor is the invention limited to the sealing of vascular organs. For example, it may be used to seal an opening formed in the thecal sac. The novel apparatus has utility in sealing openings formed by any means in any mammalian soft or hard tissue.

It may also be used to seal surgical sites of the type created during arthroscopic, endoscopic, or laporoscopic procedures conducted on the knee, back, and neck, for example. The diameter of the expandable, bioabsorbable plug would be increased as required to fill the trocar or other device that performs the role of a coaxial needle.

As an additional example, the novel plug may be employed to seal an incision of a femoral artery.

Plug 22 is formed of a bioabsorbable material so that it is bioabsorbed by the body as the opening heals. Since people heal at different rates, a bioabsorbable material should be selected so that it is fully bioabsorbed in a period of time such as a few weeks to a few months.

Examples of suitable bioabsorbable materials that expand when contacted by water include hydrogels, collagen, polysalactic acid, and any other suitable hydrophilic agents.

Examples of polymers that swell in the presence of aqueous fluids such as biological fluids will now be disclosed. Virtually all of the following polymers are hydrogels. Synthetic hydrogels can be prepared from the following classes of polymers and these are generally considered to be non-biodegradable:poly(hydroxyalkyl methylacrylates) such as poly(glyceryl methacrylate)poly(acrylamide) and poly(methacrylamide) and derivativespoly(N-vinyl-2-pyrrolidone)anionic and cationic hydrogelspoly(vinyl alcohol)poly(ethylene glycol) diacrylate and derivatives from block copolymers composed of poly(ethylene oxide)-poly(propylene oxide)-poly(ethylene oxide) and poly(propylene oxide)-poly(ethylene oxide)-poly(propylene oxide) blocks, respectively; All of the above can be cross-linked with agents such as ethylene glycol dimethacrylate or methylene-bis-acrylamide.

Biodegradable synthetic hydrogels can be prepared from polymers such as those listed above by incorporating one or more of the following monomers: Glycolide, Lactide, e-Caprolactone, p-Dioxanone and Trimethylene Carbonate In addition, biodegradable hydrogels can be based on natural products such as the following: Polypeptides such gelatin which may be cross-linked with formaldehyde or glutaraldehyde and various other dialdehydes.

Modified chitin hydrogels, which may be prepared from partially N-deacetylated chitin which, may then be cross-linked with agents such as glutaraldehyde.

Dextran, a polysaccharide, can be derivatized with groups such as 3-acryloyl-2-hydroxypropyl esters and subsequently cross-linked by free radical copolymerization with N',N'-methylenebisacrylamide.

Starch may be similarly derivatized or using glycidyl acrylate followed by free radical cross-linking as described above.

The novel plug is also treated so that it is visible under fluoroscopy, ultrasound, X-ray, magnetic resonance imaging, computed axial tomography (CAT) scanning, and other imaging techniques. Accordingly, it may contain or be impregnated with a contrast solution containing radium, iodine, beryllium, or other contrasting agent.

The bioabsorbable material of this invention could also be fabricated in a thread-like form and used as a suture material. Alternatively, after a suture has been made using conventional suture material, the bioabsorbable material could be topically applied to the sutured area to help seal the punctures made by the suture.

Figure 8A:
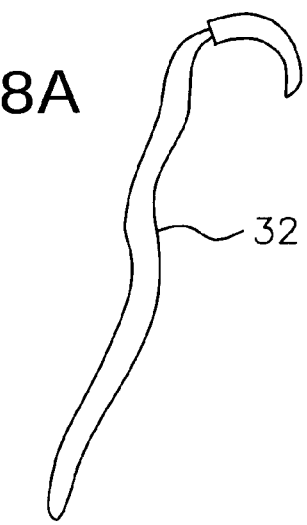
FIG. 8A is a view of a bioabsorbable suture in isolation.
Figure 8B:
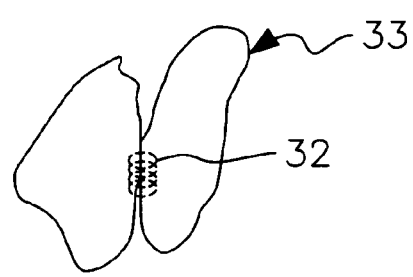
FIG. 8B is a view of a bioabsorbable suture in use to close an incision.

FIG. 8A depicts an elongate thread of suture material 32 formed of the novel dehydrated hydrogel material of this invention and FIG. 8B depicts said suture material 32 in use to close an incision formed in tissue 33.

In a first suture embodiment, suture material 32 is formed entirely of the dehydrated hydrogels of this invention. When suture material 32 comes into contact with tissue, the natural moisture within the tissue causes material 32 to expand and seal the hole created by the needle, it being understood that the needle has a diameter greater than that of the suture material 32. The body heals as the bioabsorbable suture is absorbed and no suture material remains after the holes have completely closed as a result of natural healing.

In a second embodiment, regular PGA/PLA sutures or even non-bioabsorbable sutures are coated with the novel suture material, i.e., extensible type polymers such as hydrogel that have been dehydrated. FIGS. 8A and 8B should also be interpreted as depicting this second embodiment. The coating expands upon contact with the moisture in the tissue. The non-bioabsorbable suture underlying the bioabsorbable suture material will remain, of course, after the bioabsorbable material has been absorbed but the body's natural healing process will have sealed the holes around the suture. Where a regular PGA/PLA suture is coated, it too will bioabsorb as the coating is bioabsorbed.

Advantageously, the body's natural moisture, in most applications, will cause the suture or the suture coating to expand to fill the space around it created by the larger diameter of the needle. This eliminates the need to apply an adhesive over the sutures and thus eliminates the step of curing the adhesive.

Figure 9A:
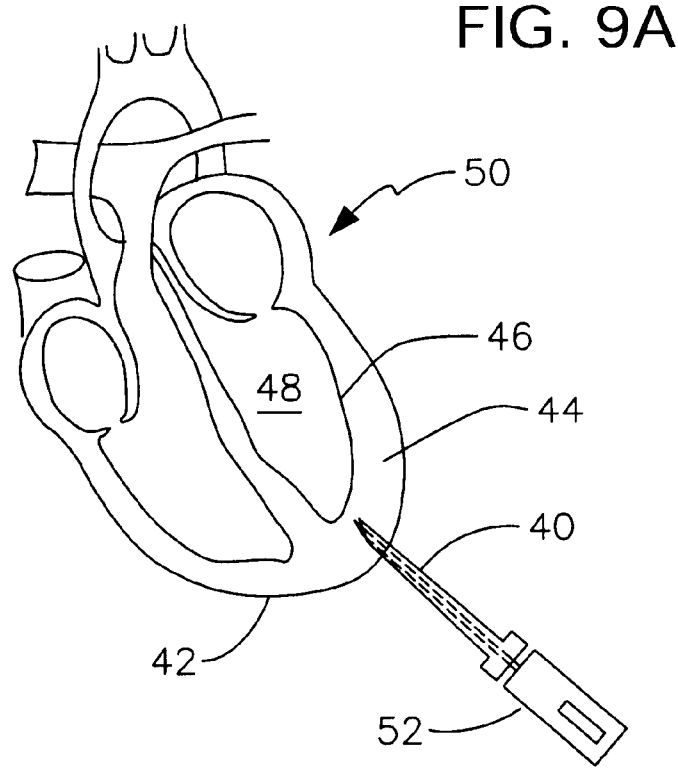
FIG. 9A is a view depicting the formation of a blind bore or core in the myocardium of a mammalian heart.

FIGS. 9A–9G disclose how the novel plugs can be used to fill cavities formed in heart tissue to promote angiogenesis in heart patients. Growth factor, stem cells, or the like are placed in the cavities or blind bores and sealed therein by means of the novel plugs disclosed herein. In FIG. 9A, coaxial needle 40 is depicted in penetrating relation to epicardium 42 and myocardium 44. Endocardium 46 is not penetrated to avoid puncturing left ventricle 48 of heart 50 in this particular example. Biopsy needle 52 is inserted through the lumen of coaxial needle 40 to remove a core of tissue from myocardium 44. This creates a blind bore in myocardium 44.

Figure 9B:
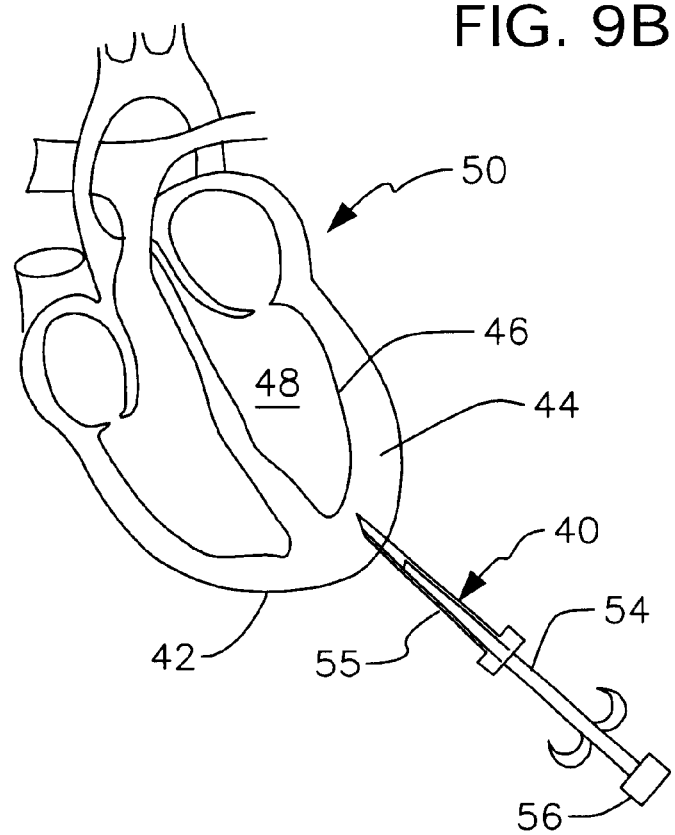
FIG. 9B is a view depicting the injection of growth factors into the blind bore.

Biopsy needle 52 is then removed from the lumen of coaxial needle 40 and a delivery sheath 54 is inserted into the lumen of said coaxial needle as depicted in FIG. 9B. Growth factor 55 such as vascular endothelial growth factor, stem cells, or the like are pushed into the blind bore from the lumen of delivery sheath 54 by plunger 56.

Figure 9C:
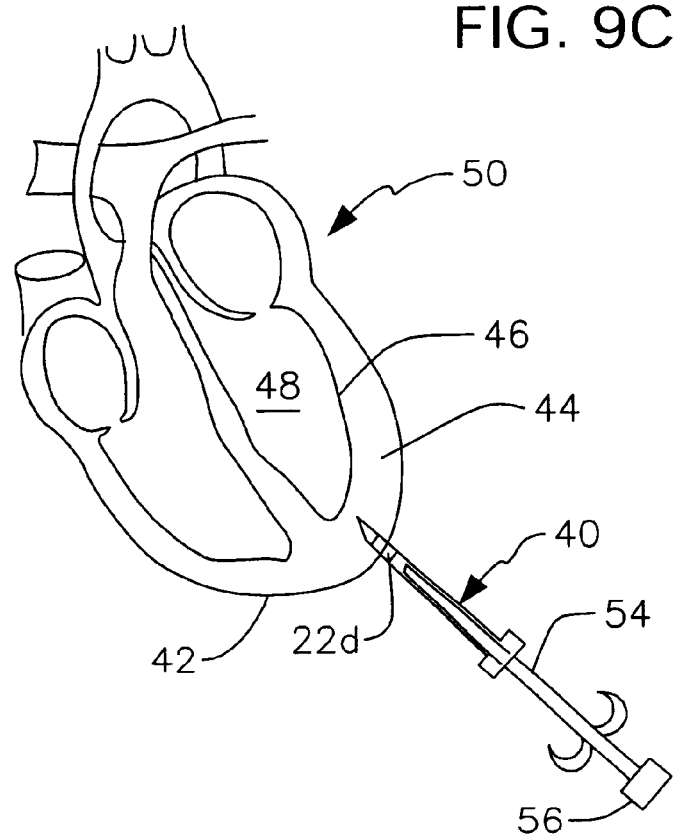
FIG. 9C is a view depicting the delivery of a bioabsorbable seal to the biopsy site.

Plunger 56 is then momentarily withdrawn from the lumen of delivery sheath 54 and a dehydrated bioabsorbable plug 22d is inserted into said lumen. Plunger 56 is then retrieved to push plug 22d into sealing relation to the blind bore as indicated in FIG. 9C.

Figure 9D:
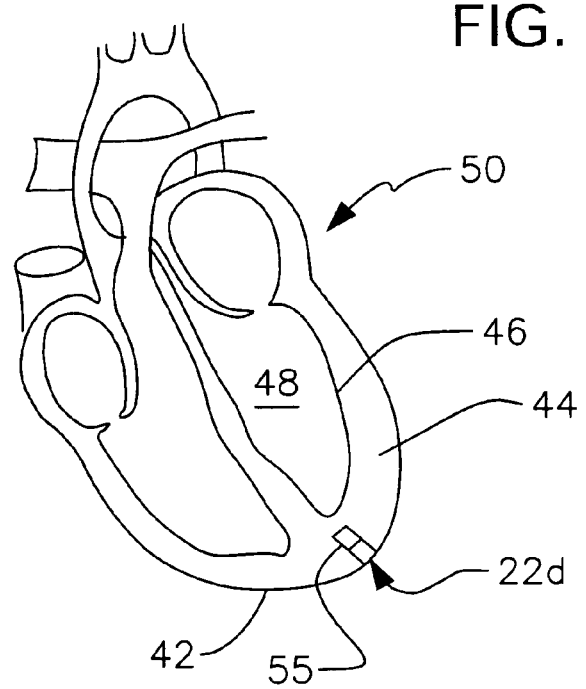
FIG. 9D depicts the bioabsorbable seal in sealing relation to the growth factor.

FIG. 9D depicts plug 22d in said sealing relation. Growth factor 55 deposited into the bottom of the blind bore is sealed therein by bioabsorbable plug 22d. Plug 22d is hydrated by the natural moisture or body fluids of the myocardium and in FIG. 9D has expanded to tightly seal the blind bore so that growth factor 55 cannot leak therefrom.

Figure 9E:
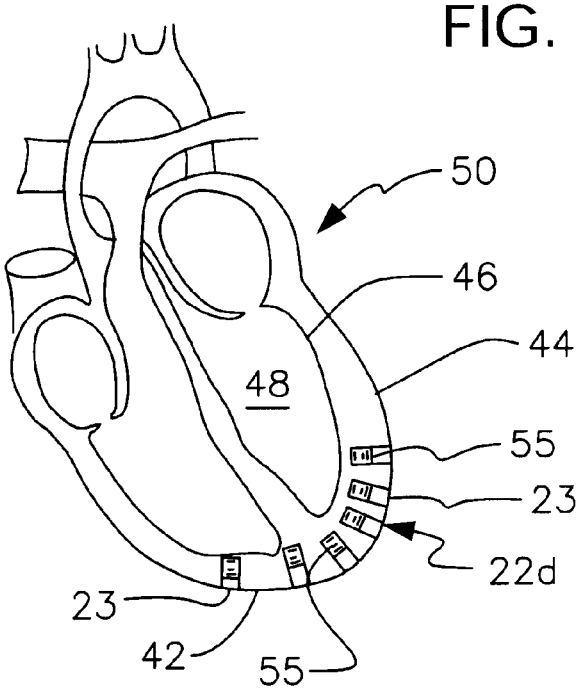
FIG. 9E depicts a plurality of blind bores filled with growth factor and sealed with the bioabsorbable plugs of this invention.

FIG. 9E depicts multiple blind bore sites filled with growth factor 55 and sealed by plugs 22d. Growth factor 55 promotes angiogenesis so that newly formed blood vessels can perform the function of dead or damaged blood vessels throughout the damaged region of the heart. Exterior surface 23 of each plug 22d is hydrophillic so that pericardium tissue does not attach to the biopsied site.

Figure 9F:
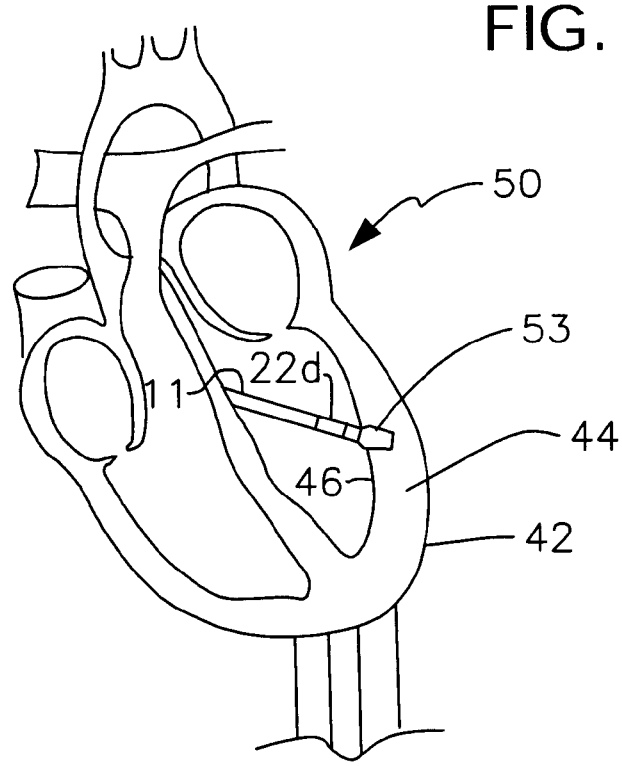
FIG. 9F depicts the formation of a cavity in the interior surface of the myocardium.
Figure 9G:
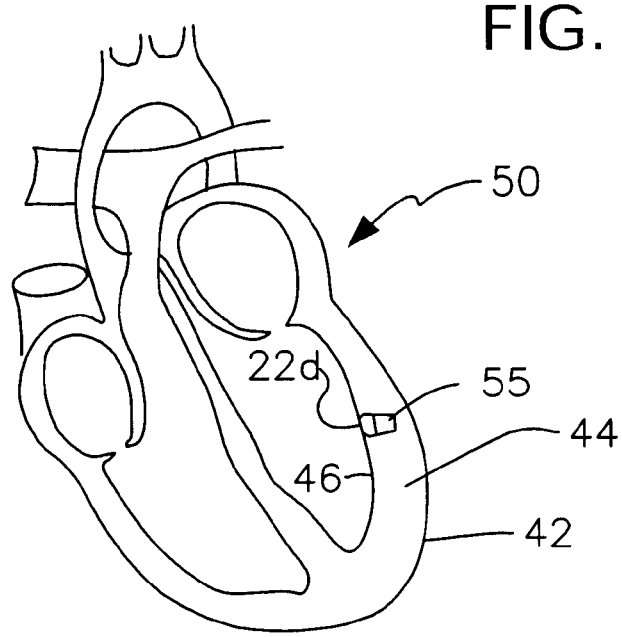
FIG. 9G depicts the plugging of the cavity of FIG. 9F with the novel bioabsorbable seal so that growth factor is sealed therein.

The blind bores or cavities can also be formed in the interior surface of the myocardium as depicted in FIGS. 9F and 9G. Cavity 53 in FIG. 9F is formed in endocardium 46 by a biopsy gun or other suitable instrument and filled with growth factor. Epicardium 42 is not punctured in this embodiment. Dehydrated bioabsorbable plug 22d is then slid into sealing relation to cavity 53 by a suitable plunger means to create the structure seen in FIG. 9G. Damaged heart tissue in the vicinity of cavity 53 is then regenerated by neovascularization. Multiple cavities 53 can be formed in the interior side of myocardium 44 as needed.

Figure 10A:
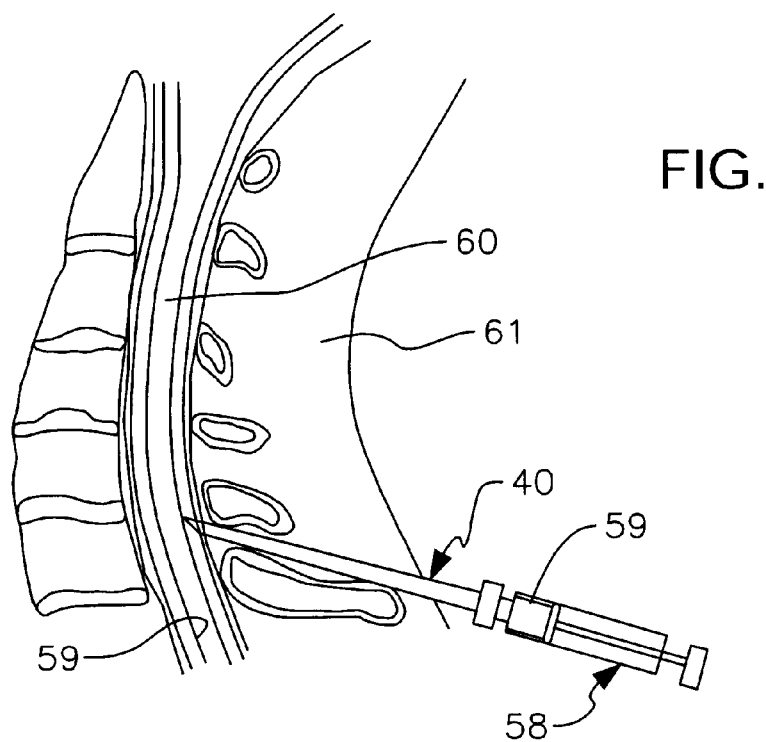
FIG. 10A is a diagrammatic view depicting puncturing of the thecal sac to withdraw cerebral spinal fluid.

FIG. 10A depicts coaxial needle 40 that receives the needle of syringe 58 used to withdraw spinal fluid 59 from spinal cord 60. Neck muscle is denoted 61.

Figure 10B:
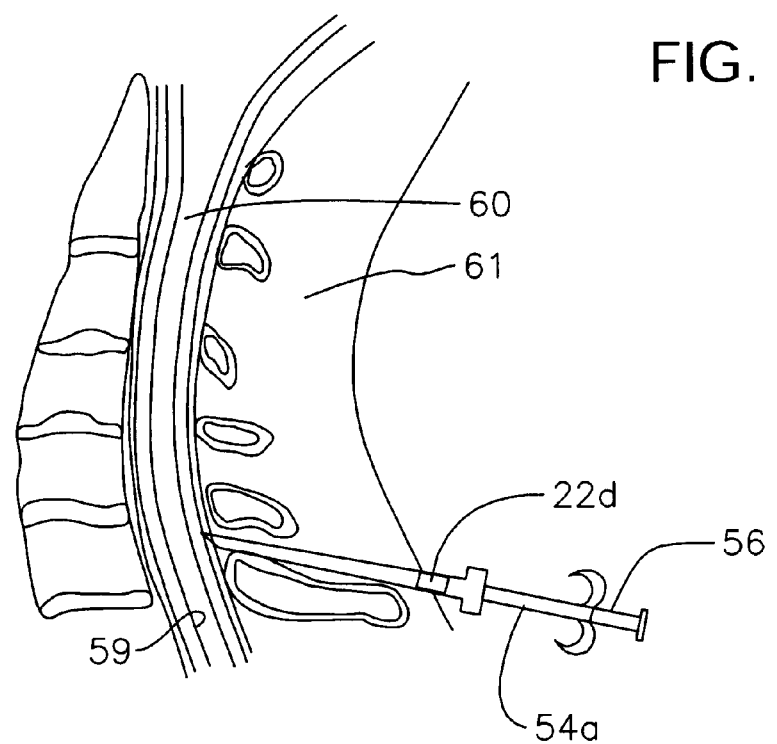
FIG. 10B is a similar view depicting the delivery of a dehydrated plug to the puncture site.

Syringe 58 is then withdrawn and as indicated in FIG. 10B, dehydrated bioabsorbable plug 22d is pushed from the lumen of delivery catheter 54 by plunger 56 into sealing relation with the opening made by the needle of syringe 58.

Figure 10C:
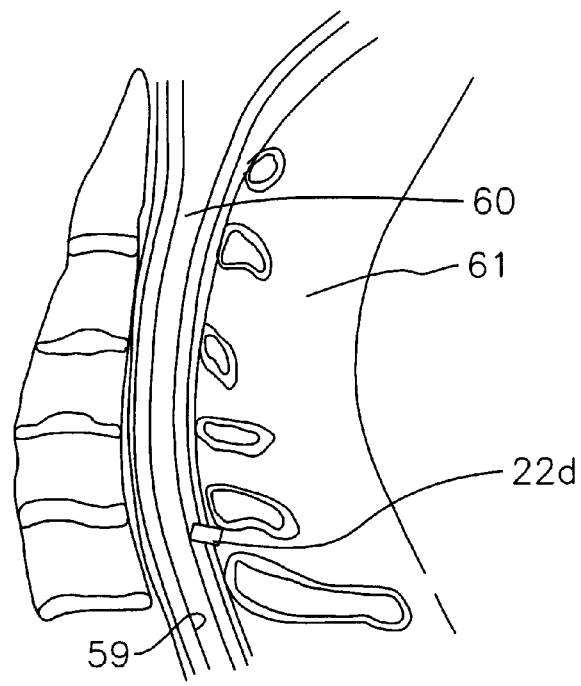
FIG. 10C depicts the hydrated plug in closing relation to the puncture formed in the thecal sac.

FIG. 10C depicts bioabsorbable plug 22d in sealing relation to the opening made by said needle. Said plug 22d is in its expanded configuration due to the natural moisture provided by spinal fluid 59, spinal cord 60, and neck muscles 61.

FIGS. 11A–11E depict how a plug of this invention may be employed to seal an incision made in an artery.

Figure 11A:
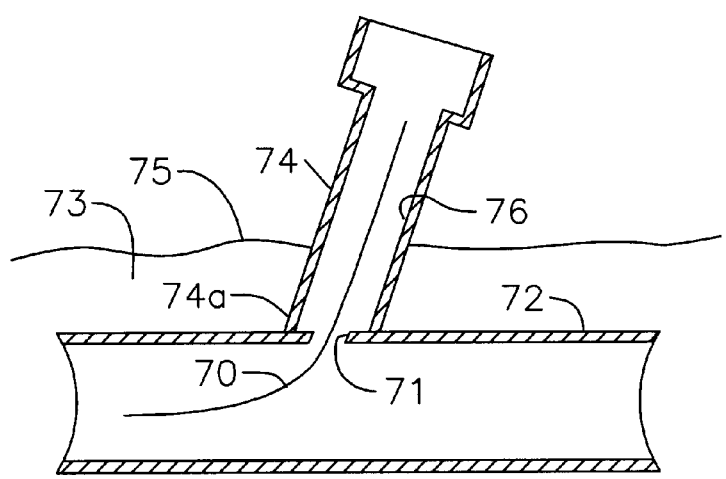
FIG. 11A is the first view in a series of animations depicting the first step of a method where an embodiment of the novel plug is used to seal an incision formed in an artery.

In FIG. 11A, guide wire 70 is depicted inserted into femoral or other artery 72 through incision 71, which may be made for diagnostic or intervention purposes. After the primary diagnostic or intervention procedures have been performed, the instruments used are removed but guide wire 70 is left in position so that it may be used as follows. Leading end 74a of introducer sheath 74 is positioned in abutting relation to artery 72 and in surrounding relation to incision 71. Reference numeral 73 denotes fat and 75 is the skin surface.

Figure 11B:
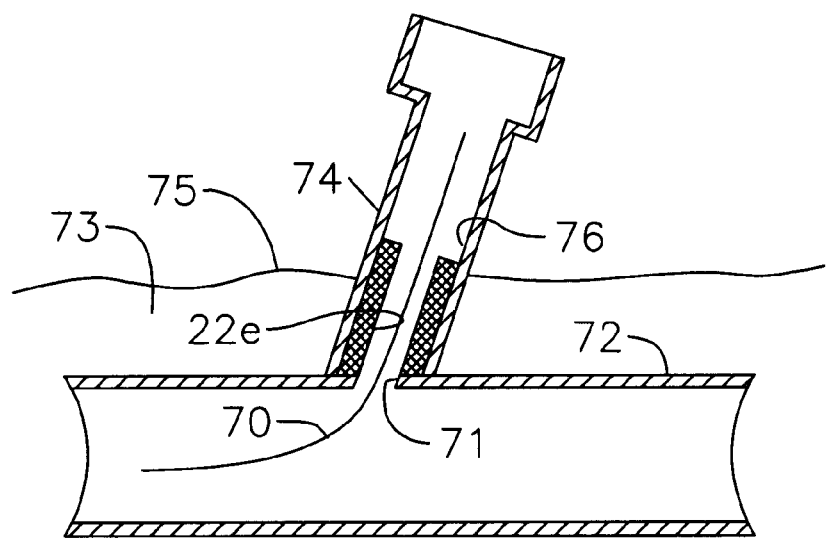
FIG. 11B is the second view in said series of animations.

A dehydrated bioabsorbable material 22e in the form of a tube is then introduced through lumen 76 of introducer sheath 74 so that its leading end also abuts artery 72 in surrounding relation to incision 71, as depicted in FIG. 11B.

Figure 11C:
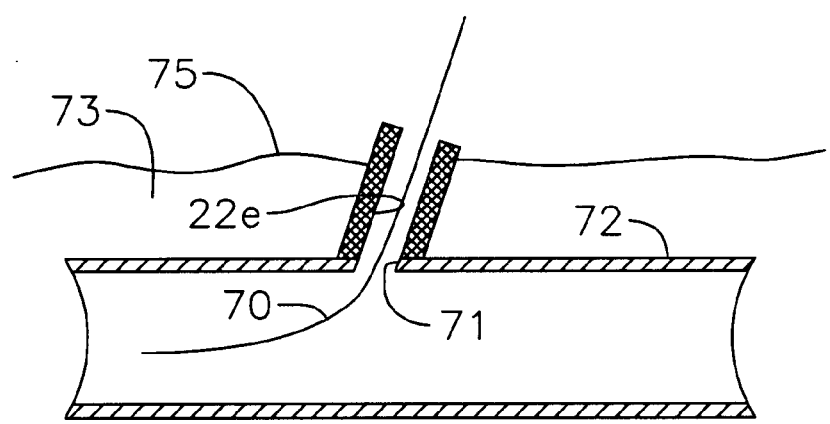
FIG. 11C is the third view in said series of animations.

Introducer sheath 74 is then withdrawn, leaving tube 22e in encircling relation to incision 71 as depicted in FIG. 11C.

Figure 11D:
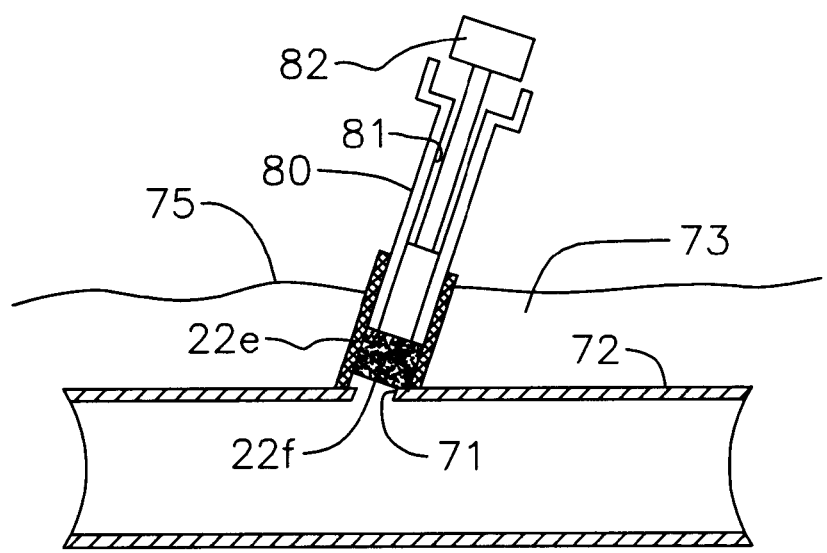
FIG. 11D is the fourth view in said series of animations.

Guide wire 70 is then removed. As indicated in FIG. 11D, an introducer sheath 80 having a smaller external diameter than introducer sheath 74 of FIG. 11B, is employed to position dehydrated plug 22f in plugging relation to tube 22e. Specifically, plug 22f is disposed in lumen 81 of introducer sheath 80 and the leading end of said introducer sheath 80 is slideably inserted into the trailing end of tube 22e as depicted. Plunger 82 is then employed to push plug 22f into tube 22e. Note that plug 22f need not abut incision 71 to accomplish its sealing function.

Figure 11E:
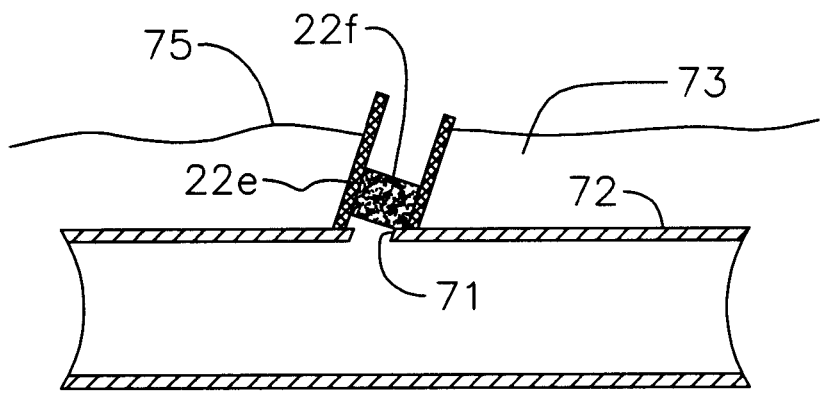
FIG. 11E is the fifth and final view in said series of animations.

FIG. 11E depicts tube 22e and plug 22f after withdrawal of introducer sheath 80 and plunger 82. Both tube 22e and plug 22f are now hydrated by the natural moisture of the body. Accordingly, both have expanded and are held in place by fat 23 and by each other. Moreover, the moisture content of the blood flowing through the artery also serves to cause the expansion of tube 22e and plug 22f. Incision 71 will heal gradually and tube 22e and plug 22f will be bioabsorbed over time. The trailing end of tube 22e that projects upwardly from the surface of skin 75 may be trimmed so that it is flush with said skin or slightly countersunk with relation thereto.

Figure 12A:
FIG. 12A is a front elevational view of a staple coated with the novel expandable and bioabsorbable material.
Figure 12B:
FIG. 12B is a front elevational view of the staple of FIG. 12A after activation.
Figure 12C:
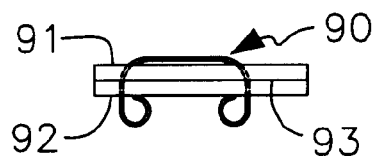
FIG. 12C is a sectional view depicting tissue on opposite sides of an incision joined to one another by the novel staple.

FIGS. 12A–12C depict the use of the novel material in the context of staples. Conventional, nonbioabsorbable staples are often used to close incisions. The staples of this embodiment are used in end-end and end-side anastomosis of organs such as the lung, the bowel, and the like. FIG. 12A depicts a staple 90 before it has been used and FIG. 12B depicts said staple 90 after activation. FIG. 12C depicts said staple when holding together two pieces of tissue 91 and 92 separated by incision 93. This embodiment requires the use of the novel material as a coating over a conventional staple because the conventional staple provides the required stiffness to enable the staple to punch through tissue layers 91, 92. The coating then expands to seal the holes created by the staple and the holes heal gradually as the bioabsorbable coating is bioabsorbed.

From the foregoing, it is apparent that the novel method includes the steps of sealing an opening of the type made by a needle or other medical or non-medical instrument by providing a plug formed of a bioabsorbable material that expands in response to a predetermined stimulus. The plug may be positioned within the lumen of a needle, a delivery sheath, or the like, and pushed therefrom by a suitable pushing means or it may installed by any other suitable method. The particular method of installation depends upon the type of opening being plugged and the particular method of application is not critical to this invention. In an exemplary embodiment involving a needle, the plug is slidingly displaced by a plunger means to a preselected location near a distal end of the lumen of the needle. Withdrawal of the needle coupled with maintaining the plug at the preselected location results in placement of the plug at the preselected location. The predetermined stimulus is then applied to cause expansion of the plug and sealing of the opening made by the needle.

Where the novel material is formed into a thread-like form for use as a suture material, or as a coating for conventional suture material which or may not be bioabsorbable, the novel method includes the steps of sewing an opening in accordance with acceptable medical procedure. In most applications, the natural moisture of the body will then cause the suture or the coating to expand radially and to thereby fill the space around it created by the larger diameter of the needle. Where insufficient moisture is present, it can simply be brushed or sprayed on in the form of a saline solution, for example. As mentioned earlier, other activating agents other than moisture are also within the scope of this invention.

Where the novel material is used as a coating for conventional staples, the novel method includes the step of using the coated staples in accordance with acceptable medical practice. The coating expands to fill openings or holes created by the staples and said coating is bioabsorbed as the opening heals.

Figure 13A:
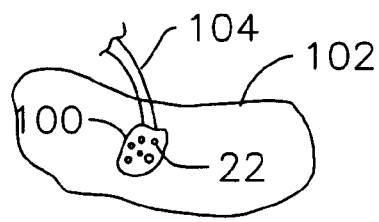
FIG. 13A is a diagrammatic view of a cavity formed in tissue being filled with the novel dehydrated bioabsorbable polymers of this invention.
Figure 13B:
FIG. 13B is a diagrammatic view depicting the cavity filled by the expanded polymers.

The novel expandable polymers also have utility in filling cavities in tissue. For example, as depicted in FIG. 13A, a cavity 100 may be formed in tissue 102 such as a liver or other organ when a tumor or lesion is removed. Catheter 104 is introduced to the site and a plurality of dehydrated plugs 22 of the novel material are pushed into cavity 100. As depicted in FIG. 13B, plugs 22 expand upon contact with naturally present moisture and fill the cavity. This prevents infections or other complications that may arise if the cavity is left unfilled.

Figure 14A:
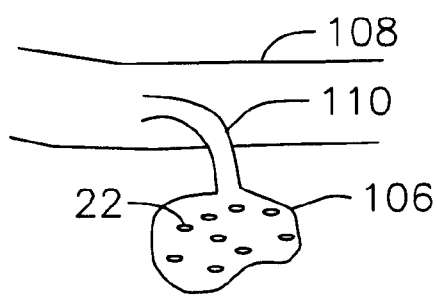
FIG. 14A is a diagrammatic view of an aneurysm being filled with the novel dehydrated bioabsorbable polymers of this invention.
Figure 14B:
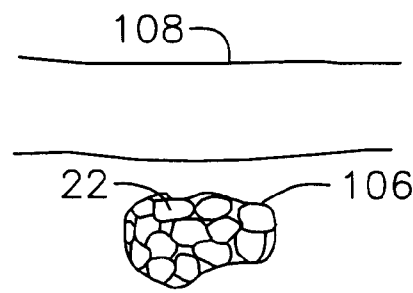
FIG. 14B is a diagrammatic view depicting the aneurysm filled by the expanded polymers.

As another example, novels plugs 22 may also be used to fill a space created by an aneurysm. In FIG. 14A, aneurysm 106 has formed a pocket adjacent artery 108. Catheter 110 is introduced into aneurysm 106 through artery 108 and a plurality of the novel plugs 22 in dehydrated condition are pushed into the aneurysm. As indicated in FIG. 14B, available natural moisture causes expansion of plugs 22 and the cavity left behind by the aneurysm is filled.

It is therefore understood that the novel plugs have utility not just in applications where an opening has been formed in the surface of tissue, but in filling cavities or other pockets within tissue as well, without regard to the cause of the cavity or pocket.

It should also be understood that there are applications where waiting for natural body fluids to activate the dehydrated plug or plugs may be contraindicated. In those applications, saline or other suitable source of moisture is injected into the lumen of the needle or catheter of other plug-delivery device before the plug is pushed therefrom and deposited into an opening or cavity. In this way, hydration of the plug begins while the plug is still undeployed so that the time required for full expansion after the plug has left the delivery device is reduced or even eliminated.

Figure 15A:
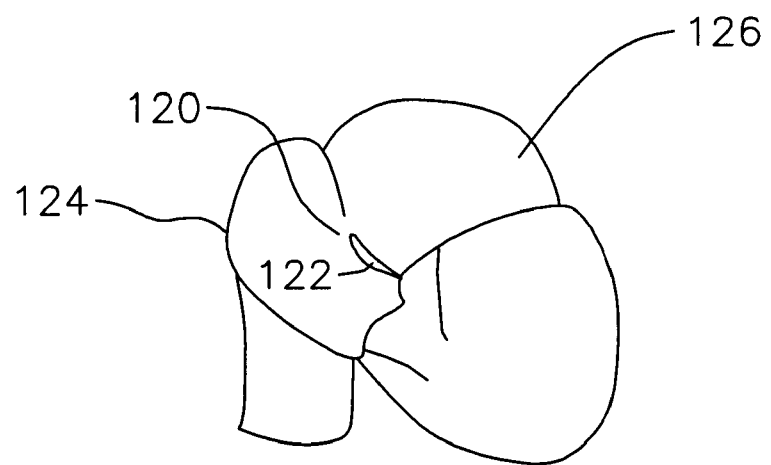
FIG. 15A diagrammatically depicts a hole in a septum of a mammalian heart.
Figure 15B:
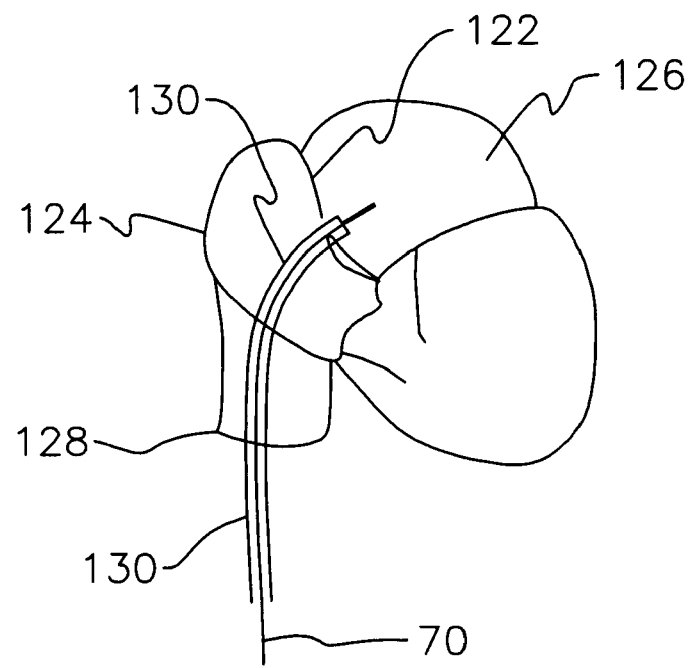
FIG. 15B is the first diagram in a four series animation depicting the novel steps for sealing said hole.

Yet another application for the novel expandable, bioabsorbable materials is in the patching of a hole or holes in a mammalian heart. In the example of FIG. 15A, a hole 120 in septum 122 unacceptably provides fluid communication between right atrium 124 and left atrium 126. As indicated in FIG. 15B, guide wire 70 is fed through femoral vein 128 so that the distal free end of guide wire 70 passes though hole 120 in septum 122 and enters into left atrium 126. A delivery catheter or sheath 130 is then fed over the guide wire until the distal free end of the sheath is also positioned within left atrium 126.

Figure 15C:
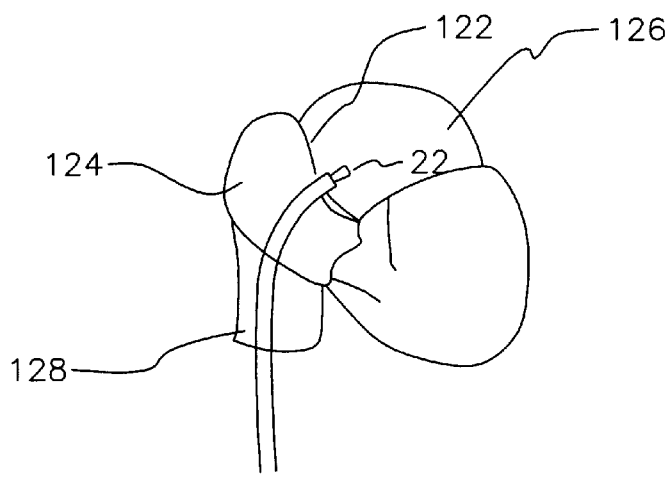
FIG. 15C is the second diagram in said series of animations.

Guide wire 70 is then removed as indicated in FIG. 15C. Plug 22 is then pushed from the lumen of sheath 130, by holding it in place with a plunger while slightly withdrawing sheath 130, until the distal free end of the plug is positioned within the left atrium. Plug 22 is allowed to expand upon contact with natural moisture in the heart. It may also be pre-hydrated by injecting saline or other suitable solution into the lumen of sheath 130 prior to deployment of plug 22 so that the expansion time is reduced or eliminated. The expansion of plug 22 in left atrium 126 provides an anchoring means so that sheath 130 can be slowly withdrawn, leaving plug 22 deployed in opening 120.

Figure 15D:
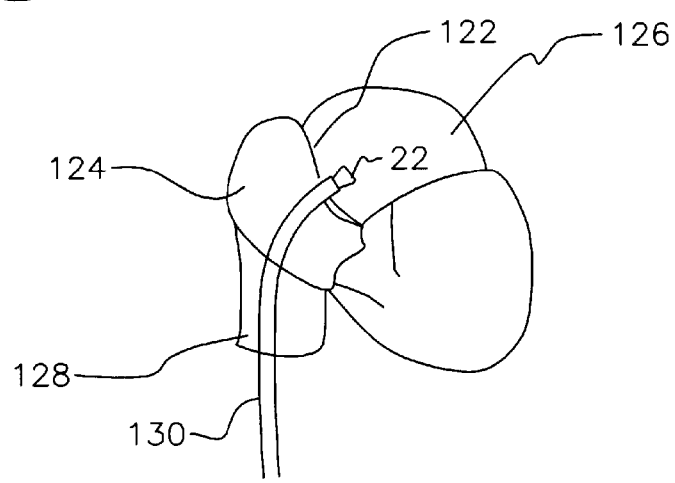
FIG. 15D is the third diagram of said series.
Figure 15E:
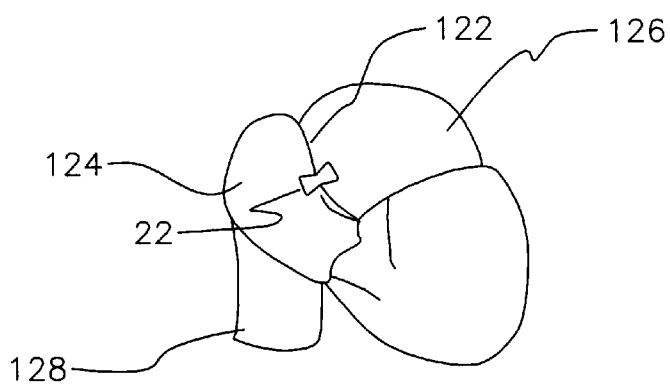
FIG. 15E is the fourth diagram of said series.

Sheath 130 is then withdrawn further as depicted in FIG. 15D so that plug 22 begins expanding in right atrium 124. Sheath 130 is then fully withdrawn as depicted in FIG. 15E. Plug 22 is now fully expanded and hole 120 is closed so that the left and right atriums are no longer in fluid communication with one another.

Plug 22 is coated or impregnated with a contrasting agent to facilitate its viewing and hence accurate placement when employing various imaging techniques, as in the embodiments described above.

A plug used to seal an opening in a heart is preferably formed of a material that is bioabsorbed very slowly over a long period of time. Plug 22 may also be impregnated with a growth factor or other therapeutic agents to promote healing.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method for sealing a puncture opening of the type made by a coaxial needle, comprising the steps of:

providing a dehydrated plug formed of hydrogel that expands in response to application of a liquid fluid thereto;

slidingly disposing the dehydrated plug in a lumen of said coaxial needle;

pre-hydrating said dehydrated plug by introducing a liquid-fluid solution into said lumen of said coaxial needle before displacing said prehydrated plug from said lumen;

slidingly displacing said prehydrated plug within said lumen to a preselected location near a distal end of said lumen;

withdrawing said coaxial needle while maintaining said prehydrated plug at said preselected location;

whereby said pre-hydrated plug expands to fill said puncture opening in less time than a dehydrated plug that is not pre-hydrated.

* * * * *